(12) United States Patent
Shubin, Sr. et al.

(10) Patent No.: US 11,786,225 B2
(45) Date of Patent: Oct. 17, 2023

(54) SYSTEMS AND METHODS RELATED TO COLLECTION OF BIOLOGICAL FLUIDS

(71) Applicant: Steven A. Shubin, Sr., Austin, TX (US)

(72) Inventors: Steven A. Shubin, Sr., Austin, TX (US); Steven A. Shubin, Jr., Santa Fe, NM (US)

(73) Assignee: Steven A. Shubin, Sr., Dripping Springs, TX (US)

( * ) Notice: Subject to any disclaimer, the term of this patent is extended or adjusted under 35 U.S.C. 154(b) by 69 days.

(21) Appl. No.: 17/132,284

(22) Filed: Dec. 23, 2020

(65) Prior Publication Data

US 2022/0192643 A1    Jun. 23, 2022

(51) Int. Cl.
  *A61B 10/00*   (2006.01)
  *A61F 5/453*   (2006.01)
  *B29C 45/00*   (2006.01)
  *B29L 31/00*   (2006.01)

(52) U.S. Cl.
  CPC .......... *A61B 10/0058* (2013.01); *A61F 5/453* (2013.01); *B29C 45/0001* (2013.01); *B29L 2031/753* (2013.01)

(58) Field of Classification Search
  CPC . A61B 10/0058; A61F 5/453; B29C 45/0001; B29L 2031/753
  See application file for complete search history.

(56) References Cited

U.S. PATENT DOCUMENTS

| | | |
|---|---|---|
| 5,466,235 A | 11/1995 | Shubin, Sr. |
| 5,782,818 A | 7/1998 | Shubin |
| 5,806,523 A | 9/1998 | Shubin, Sr. |
| 5,807,360 A | 9/1998 | Shubin |
| D703,678 S | 4/2014 | Shubin, Sr. |
| D704,201 S | 5/2014 | Shubin, Sr. |
| D706,274 S | 6/2014 | Shubin, Sr. |
| D724,204 S | 3/2015 | Shubin, Sr. et al. |
| D726,308 S | 4/2015 | Shubin, Sr. et al. |
| 9,039,600 B2 | 5/2015 | Shubin, Sr. et al. |
| D732,662 S | 6/2015 | Shubin, Sr. et al. |
| 9,254,121 B2 | 2/2016 | Shubin, Sr. et al. |
| D751,694 S | 3/2016 | Shubin, Sr. et al. |
| 9,597,060 B2 | 3/2017 | Shubin, Sr. et al. |
| 9,949,866 B2 | 4/2018 | Shubin, Sr. |
| 2013/0253457 A1* | 9/2013 | Shubin, Sr. ............. A61F 5/453 604/349 |
| 2016/0374848 A1* | 12/2016 | Sanchez ................. A61F 5/453 604/319 |
| 2018/0022018 A1 | 1/2018 | Cambridge |

\* cited by examiner

*Primary Examiner* — Adam Marcetich
*Assistant Examiner* — Rachel O'Connell
(74) *Attorney, Agent, or Firm* — Dickinson Wright PLLC

(57) ABSTRACT

Collection of biological fluids. At least one example is a polymeric sleeve including: an elongate body that defines a main passageway; an internal chamber defined within the main passageway; a first flange suspended within the internal chamber at a first position along the longitudinal central axis; and an aperture through the first flange, the aperture at least partially aligned with the longitudinal central axis.

11 Claims, 9 Drawing Sheets

SYSTEMS AND METHODS RELATED TO COLLECTION OF BIOLOGICAL FLUIDS

CROSS-REFERENCE TO RELATED APPLICATIONS

Not Applicable.

BACKGROUND

In recent years there have many advancements in devices for stimulation and collection of biological fluids, particularly seminal fluids. For example, FLESHLIGHT® brand products are devices that aid in stimulation and collection of seminal fluids through ejaculation. Many such products visually mimic genitalia, and also attempt to simulate the feel of copulation.

Studies have found that prostate health in human males may be related to frequency of ejaculation. In particular, infrequent ejaculation can lead to swelling of the prostate, known as congestive prostatitis, and may also increase the cancer risk in human males. Some medical sources suggest an ejaculation frequency of three to four times per week ensures good prostate health and reduces cancer risk. One study found a 14% lower lifetime prostate cancer rate for men who ejaculate between 13 and 20 times per month, and an upwards of 33% lower lifetime prostate cancer risk for men who ejaculate 21 times or more each month. Devices for stimulation and collection of seminal fluids may aid in achieving higher ejaculations rates among men.

Beyond the prostate health effects of ejaculation, devices for stimulation and collection of seminal fluids through ejaculation may also assist in reversing desensitization issues. That is, repeated masturbatory stimulation of the penis using the hand or rough cloth can lead to desensitization of the penis, particularly in the absence of lubrication. Desensitization can then result in erectile dysfunction during copulation. Use of properly lubricated devices designed specifically for the stimulation and collection of seminal fluid may help reverse the desensitization issues, and thus reduce the occurrence of erectile dysfunction related to desensitization issues.

Any improvement in devices for stimulation and collection of seminal fluid, in view of the positive health benefits, would be beneficial.

SUMMARY

One example is a system comprising a polymeric sleeve. The polymeric sleeve may comprise: an elongate body that defines a first end, a second end opposite the first end, and a longitudinal central axis; a main passageway through the elongate body along the longitudinal central axis, the main passageway extends from the first end to the second end, and the main passageway defines a first aperture on the first end and a second aperture on the second end; an internal chamber defined within the main passageway between the first aperture and the second aperture; a first flange disposed within the internal chamber at a first position along the longitudinal central axis, the first flange defines an aperture at least partially aligned with the longitudinal central axis; a first stanchion extending from the first flange along a first radial direction relative to the longitudinal central axis, the first stanchion coupled to an inside surface of the internal chamber; a second stanchion extending from the first flange along a second radial direction relative to the longitudinal central axis, the second stanchion coupled to an inside surface of the internal chamber; and the first and second stanchions suspend the first flange within the internal chamber.

The example system may further comprise a first interstitial volume defined between the inside surface of the internal chamber, the first stanchion, and the second stanchion.

In the example system the first radial direction and the second radial direction may form an angle of at least 90 angular degrees. In the example system the first radial direction and the second radial direction may form an angle of 180 angular degrees.

The example system may further comprise a third stanchion extending from the first flange along a third radial direction relative to the longitudinal central axis, the third stanchion coupled to the inside surface of internal chamber. In the example system: the first radial direction and the second radial direction form an angle of 120 angular degrees; and the second radial direction and the third radial direction form an angle of 120 angular degrees.

The example system may further comprise: a first interstitial volume defined between the inside surface of the internal chamber, the first stanchion, and the second stanchion; a second interstitial volume defined between the inside surface, the second stanchion, and third stanchion; and a third interstitial volume defined between the inside surface, the third stanchion, and the first stanchion.

The example system may further comprise: a second flange disposed within the internal chamber at a second position along the longitudinal central axis; a third stanchion extending from the second flange along a third radial direction relative to the longitudinal central axis, the third stanchion coupled to the inside surface; a fourth stanchion extending from the second flange along a fourth radial direction relative to the longitudinal central axis, the fourth stanchion coupled to the inside surface; and the third and fourth stanchions suspend the second flange within the internal chamber.

The example system may further comprise: a third stanchion extending from the first flange along a third radial direction relative to the longitudinal central axis, the third stanchion coupled to the inside surface; a second flange disposed within the internal chamber at a second position along the longitudinal central axis; a fourth stanchion extending from the second flange along a fourth radial direction relative to the longitudinal central axis, the fourth stanchion coupled to the inside surface; a fifth stanchion extending from the second flange along a fifth radial direction relative to the longitudinal central axis, the fifth stanchion coupled to the inside surface; and a sixth stanchion extending from the second flange along a sixth radial direction relative to the longitudinal central axis, the sixth stanchion coupled to the inside surface. The example system may further comprise: the first radial direction and the second radial direction may form an angle of 120 angular degrees; the second radial direction and the third radial direction may form an angle of 120 angular degrees; the fourth radial direction and the fifth radial direction may form an angle of 120 angular degrees; the fifth radial direction and the sixth radial direction may form an angle of 120 angular degrees; and the first radial direction and the third radial direction may form an angle of 60 angular degrees.

The example system may further comprise an outer cover of rigid material that defines an interior volume, wherein the polymeric sleeve is at least partially disposed within the outer cover.

Another example is a method of making a polymeric sleeve comprising: placing a lower mold component, the lower mold component structurally defines a negative image of an insertion end of the polymeric sleeve, and the lower mold component defines a negative image of a first portion of a main passageway of the polymeric sleeve; assembling into mating relationship a disk assembly, the disk assembly structurally defines a negative image of an internal volume of the polymeric sleeve, and the disk assembly defines a negative image of at least two stanchions and a first flange; stacking the disk assembly into mating relationship with the lower mold component; coupling a rod member to the disk assembly, an exterior surface of the rod member defines a negative image of the main passageway from the internal volume to a vent end of the polymeric sleeve; closing an outer mold assembly around the disk assembly and rod member, an interior surface of the outer mold assembly structurally defines a negative image of an outer surface of the polymeric sleeve; and injecting a polymeric compound in a liquid state into the outer mold assembly.

In the example method, the assembling may further comprise abutting a lower disk member against an upper disk member. In the example method, the lower disk member and the upper disk member, when assembled, define a negative image of a first stanchion at a first radial direction, a second stanchion at a second radial direction and a third stanchion at a third radial direction.

In the example method, the assembling may further comprise: abutting a lower disk member against a medial disk member, and abutting the medial disk member against an up upper disk member; the lower disk member and medial disk member define the negative image of at least two stanchions and the first flange; and the medial disk member and the upper disk member define a negative image of at least two stanchions and a second flange.

In the example method, the assembling may further comprise: abutting a lower disk member against a medial disk member, and abutting the medial disk member against an up upper disk member; the lower disk member and medial disk member defines a negative image of three stanchions and the first flange; and the medial disk member and the upper disk member define a negative image of three stanchions and a second flange.

Another example is a mold system for creating a polymeric sleeve, the mold system comprising: a lower mold defining a mold surface and a stem that protrudes upward from the mold surface along a longitudinal axis; a disk assembly configured to stack into mating relationship with an upper end of the stem, the disk assembly defining at least two channels into a first interior volume that circumscribes the longitudinal axis; and a rod configured to couple to an upper surface of the disk assembly and extend along the longitudinal axis.

In the example mold assembly, the disk assembly may further comprise a lower disk member and an upper disk member, the lower and upper disk members defining three channels into the interior volume, the three channels extending along three distinct radial directions relative to the longitudinal axis.

In the example mold assembly, the disk assembly may further comprise: a lower disk member abutting a medial disk member, and the medial disk member abutting an upper disk member; the lower disk member and medial disk member defining at least two channels into the first interior volume; and the medial disk member and the upper disk member defining at least two channels into a second interior volume, the second interior volume circumscribing the longitudinal axis.

In the example mold assembly, the disk assembly may further comprise: a lower disk abutting a medial disk member, and the medial disk member abutting an upper disk member; the lower disk member and medial disk member defining a first, second, and third channels into the first interior volume, the first, second, and third channels extending along a first, second, and third radial directions, respectively; and the medial disk member and upper disk member defining a fourth, fifth, and sixth channels into a second interior volume that circumscribes the longitudinal axis, the fourth, fifth, and sixth channels extending along a fourth, fifth, and sixth radial directions, respectively. In the example mold assembly, the first radial direction may be 60 angular degrees from the fourth radial direction.

BRIEF DESCRIPTION OF THE DRAWINGS

For a detailed description of example embodiments, reference will now be made to the accompanying drawings in which.

DEFINITIONS

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

"About" in reference to number (e.g., a length or a width) shall mean the recited number plus or minus ten percent (+/−10%) of the recited number.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The various embodiments are directed to systems and methods of creating polymeric sleeves for collection of biological fluids, particularly seminal fluid. The various example systems were developed in the context of devices for use by human males, and thus the description that follows is based on the developmental context; however, the systems and methods may find other uses, such as veterinary uses (e.g., horses, dogs), and thus the developmental context shall not be viewed as a limitation as to the scope of the applicability of the devices.

Figure 1:
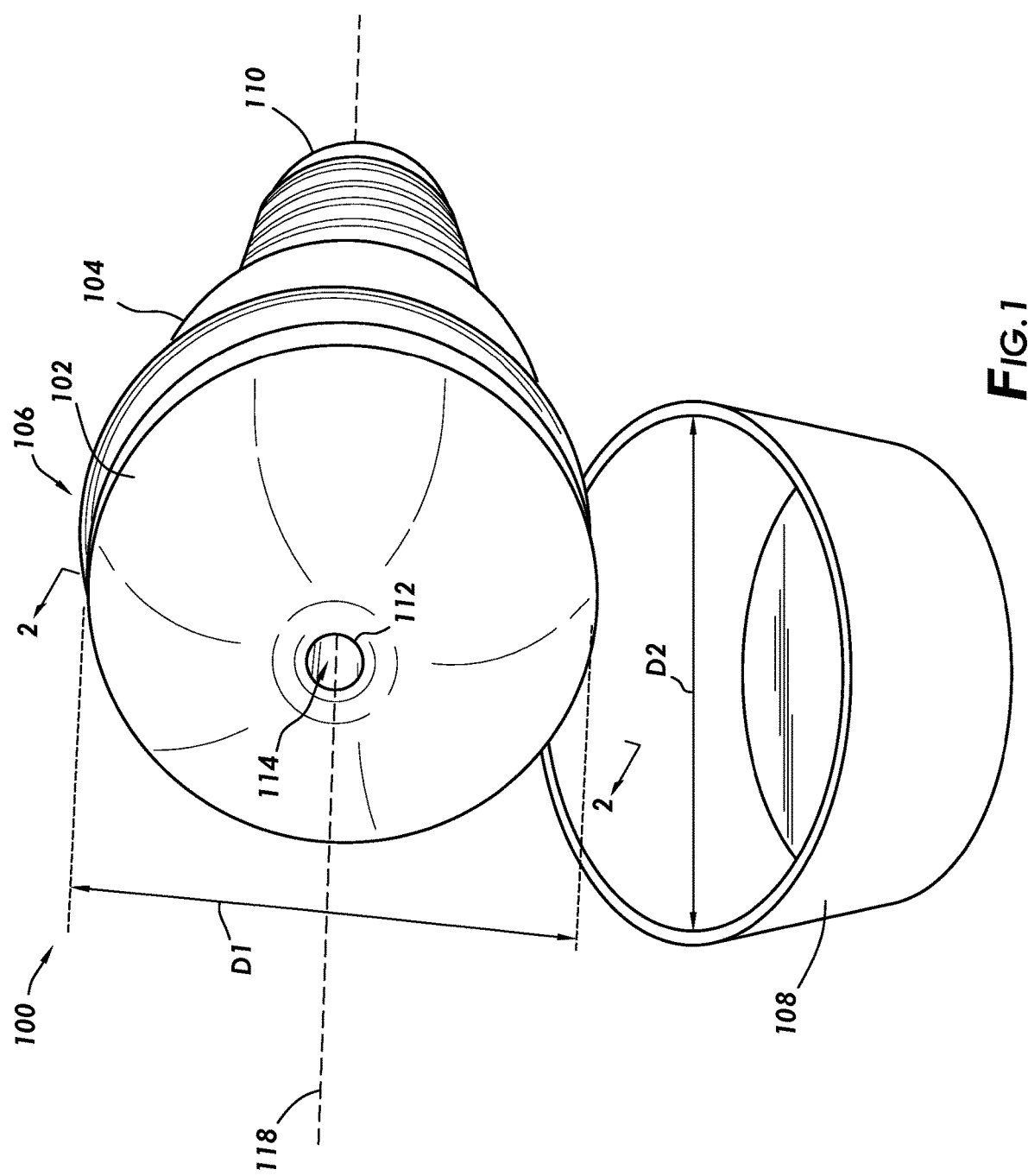
FIG. 1 shows a perspective view of system in accordance with at least some embodiments.

FIG. 1 shows a perspective view of system 100 in accordance with at least some embodiments. In particular, the system 100 comprises a polymeric sleeve 102 at least partially disposed within an interior volume of an outer cover 104 of rigid material, such as plastic. In the view of FIG. 1, only the insertion end 106 of the polymeric sleeve 102 is visible, as the balance of the polymeric sleeve resides within the outer cover 104. The polymeric sleeve 102 may be made of a thermoplastic elastomer gel (TPE) of low durometer rating, or other material, such as silicon, polyvinyl chloride (PVC), or elastomeric rubber. The system 100 may further comprise a cover or lid 108 that defines an inside diameter D2 slightly larger than the outside diameter of the D1 of the insertion end 106 of the polymeric sleeve 102 such that, when not in use, the lid 108 may be telescoped over the insertion end 106 and couple to the outer cover 104. The lid 108 may, for example, protect the insertion end 106 from damage when not in use. The system 100 may further comprise a second cap or lid 110 that couples to the outer cover 104 opposite the lid 108. The lid 110 may act, in some cases and in conjunction with other features of the outer cover 104, as a controllable vent mechanism during use. The diameter D1 may be about 3.0 inches, and the diameter D2 may be slightly larger to accommodate telescoping over the insertion end 106.

The insertion end 106 of the example system 100 comprises a main aperture 112 which leads to a main passageway 114 (only partially visible in FIG. 1, but discussed more below). The main passageway 114 is aligned with a longitudinal central axis 118 of the polymeric sleeve 102. In some cases, the main passageway 114 may be coaxial with the longitudinal central axis 118. In other cases, the main passageway 114 may be parallel to but offset slightly from the longitudinal central axis 118.

Figure 2:
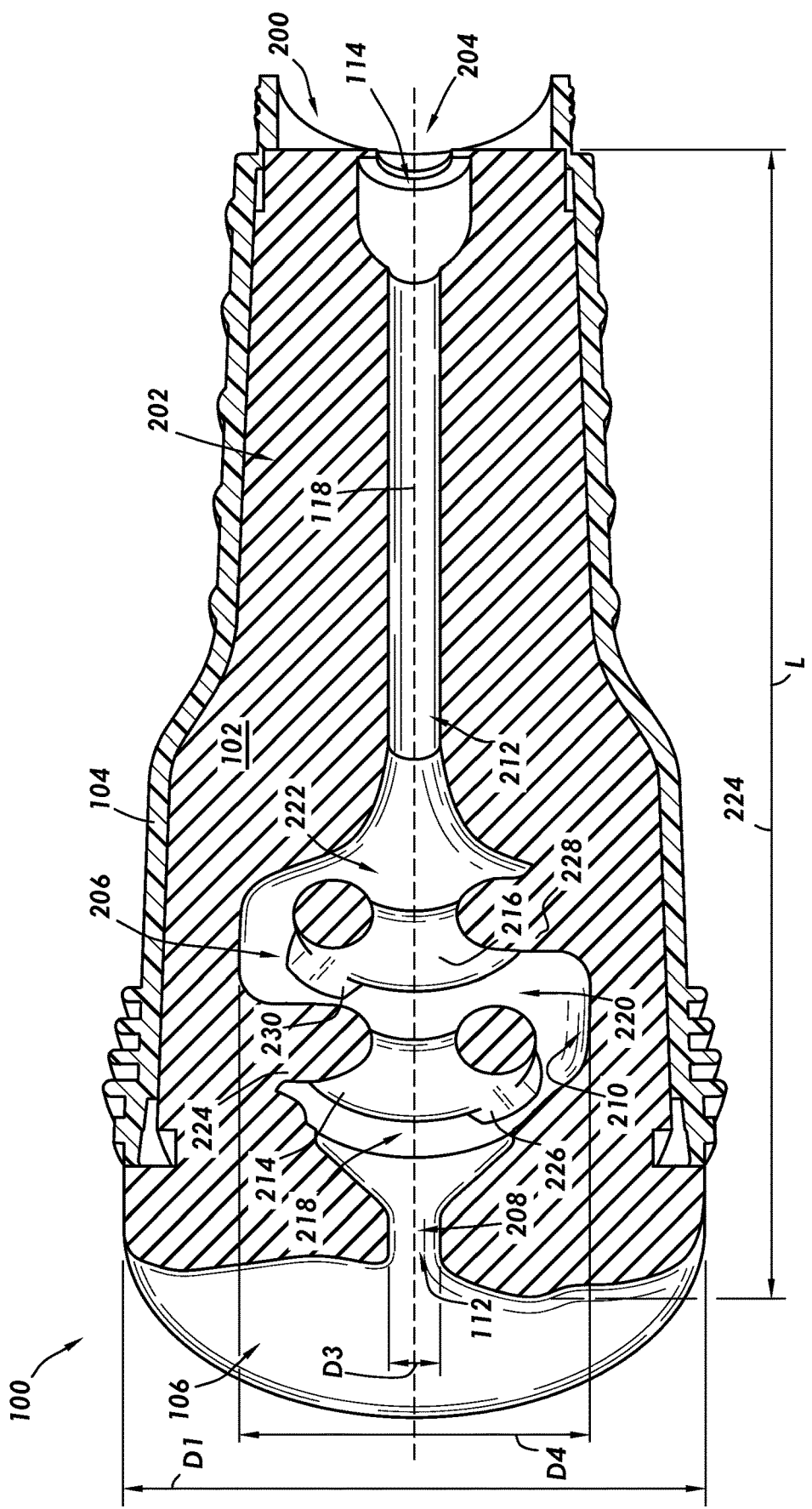
FIG. 2 shows a cross-sectional perspective view, taken substantially along line 2-2 of FIG. 1, in accordance with at least some embodiments.

FIG. 2 shows a cross-sectional perspective view of the system 100 of FIG. 1, taken substantially along line 2-2 of FIG. 1. In particular, FIG. 2 shows a portion of the outer cover 104 and the polymeric sleeve 102. The outer cover 104 defines an internal volume 200 as well as the longitudinal central axis 118. The polymeric sleeve 102 is partially disposed within the internal volume 200. In the example system shown, the insertion end 106 resides at least partially outside the internal volume 200 of the outer cover 104. The polymeric sleeve 102 defines an elongate body 202 and a vent end 204 opposite the insertion end 106. In some example systems, the overall length L is at least two times the diameter D1, in some cases about three times the diameter D1, and in a particular case about nine inches.

The main passageway 114 runs from the insertion end 106 to the vent end 204 along the longitudinal central axis 118. Better visible in FIG. 2 is the fact the main passageway 114 defines the main aperture 112 on the insertion end 106. An internal cavity or internal chamber 206 resides along the main passageway 114, and the internal chamber 206 may be disposed at the wider end of the polymeric sleeve 102. In particular, working from left to right in FIG. 2, the main passageway 114 comprises a first portion 208 that runs from the main aperture 112 to the internal chamber 206. The first portion 208 has diameter D3, in some cases about 0.5 inches. The first portion 208 is fluidly coupled to the internal chamber 206 that has a diameter D4. In some cases, the diameter D4 is at least twice the diameter D3, and in a particular case the diameter D4 is about four times the diameter D3. The internal chamber 206 defines an inside wall or inside surface 210. The main passageway 114 then comprises a second portion 212 that ends from the internal chamber 206 to the vent end 204. In some cases, the second portion 212 has a diameter about the same as the first portion 208, but in any event the diameter of the second portion is smaller than the diameter D4 of the internal chamber 206. The inside surface of the second portion 212 may be smooth in some cases, and in other cases the inside surface of the second portion 212 may be textured to increase stimulation. For example, the second portion may include inward projecting features, such as "rifling", various tabs, or protrusions.

In accordance with various embodiments, one or more suspended rings or flanges reside within the internal chamber 206. In the example system of FIG. 2, two flanges are present—a proximal flange 214 and a distal flange 216. The proximal flange 214 is disposed at a first position relative to the longitudinal central axis 118, the first position closer to the insertion end 106. The distal flange 216 is disposed at a second position relative to the longitudinal central axis 118, the second position closer to the vent end 204. The proximal flange 214 and distal flange 216 conceptually divide the internal chamber 206 into a proximal volume 218, a medial volume 220, and a distal volume 222. While two flanges 214 and 216 are shown, one or more flanges may be implemented (e.g., only one flange, exactly three flanges), and thus showing a system with two flanges shall not be read as a limitation.

Still referring to FIG. 2, and particularly the proximal flange 214. The example proximal flange 214 takes the form of a ring or toroid. More particularly, the example proximal flange 214 takes the form of a torus. However, any shape suitable to be suspended within the internal chamber 206 may be used, such as a toroid with the square cross-section. The example proximal flange 214 has a thickness, measured parallel to the longitudinal central axis 118, of about 0.75 inches. The example proximal flange 214 is suspended in the internal chamber 206 by way of a plurality of braces, stays, or stanchions. In the example system 100 of FIG. 2, three stanchions are associated with the proximal flange 214, though in the cross-sectional view of FIG. 2 only two are visible. In particular, a first stanchion 224 is shown in cross-section. The stanchion 224 extends from the proximal flange 214 along a first radial direction relative to the longitudinal central axis 118. The stanchion 224 is coupled to the inside surface of the internal chamber 206. A second stanchion 226 is also visible in the cross-sectional perspective view of FIG. 2. The stanchion 226 extends from the proximal flange 214 along a second radial direction relative to the longitudinal central axis 118. The stanchion 226 is also coupled to an inside surface of the internal chamber 206. In the example system, a third stanchion would also be associated with the proximal flange 214, but the third stanchion is not visible because of the cross-sectional view. All the stanchions (e.g., stanchions 224 and 226) for the proximal flange 214 reside at the same longitudinal position along the longitudinal central axis 118, but each stanchion extends along a different radial direction from the longitudinal central axis 118.

Now referring to distal flange 216. The distal flange 216 takes the form of a ring or toroid. More particularly, the distal flange 216 takes the form of a torus. However, any shape suitable to be suspended within the internal chamber 206 may be used, such as a toroid with the square cross-section. Moreover, the proximal flange 214 and the distal flange 216 need not match. The example distal flange 216 has a thickness, measured parallel to the longitudinal central axis 118, of about 0.75 inches, though the distal flange 216 and proximal flange 214 need not have the same thickness. The example distal flange 216 is suspended in the internal chamber 206 by way of a plurality of braces, stays, or stanchions. In the example system 100 of FIG. 2, three stanchions are associated with the distal flange 216. In the cross-sectional view of FIG. 2, two of the three stanchions associated with the distal flange 216 are visible. In particular, a first stanchion 228 is shown in cross-section. The stanchion 228 extends from the distal flange 216 along a third radial direction relative to the longitudinal central axis 118. The stanchion 228 is coupled to the inside surface of the internal chamber 206. A second stanchion 230 is also visible in the cross-sectional view of FIG. 2. The stanchion 230 extends from the distal flange 216 along a fourth radial direction relative to the longitudinal central axis 118. The stanchion 230 is also coupled to an inside surface of the internal chamber 206. In the example system, a third stanchion would also be associated with the distal flange 216, but the third stanchion is not visible because of the cross-sectional view.

The stanchions (e.g., 224, 226, 228, and 230) each extend along a radial direction different than the radial direction of other stanchions associated with the particular flange. Moreover, in the example system 100, as between the flanges, each stanchion extends in a different radial direction. However, as between the flanges, and given the offset between the flanges along the longitudinal central axis 118, the stanchions may extend along about the same radial directions without adversely affecting the casting or molding of the polymeric sleeve 102, or its use.

Figure 3:
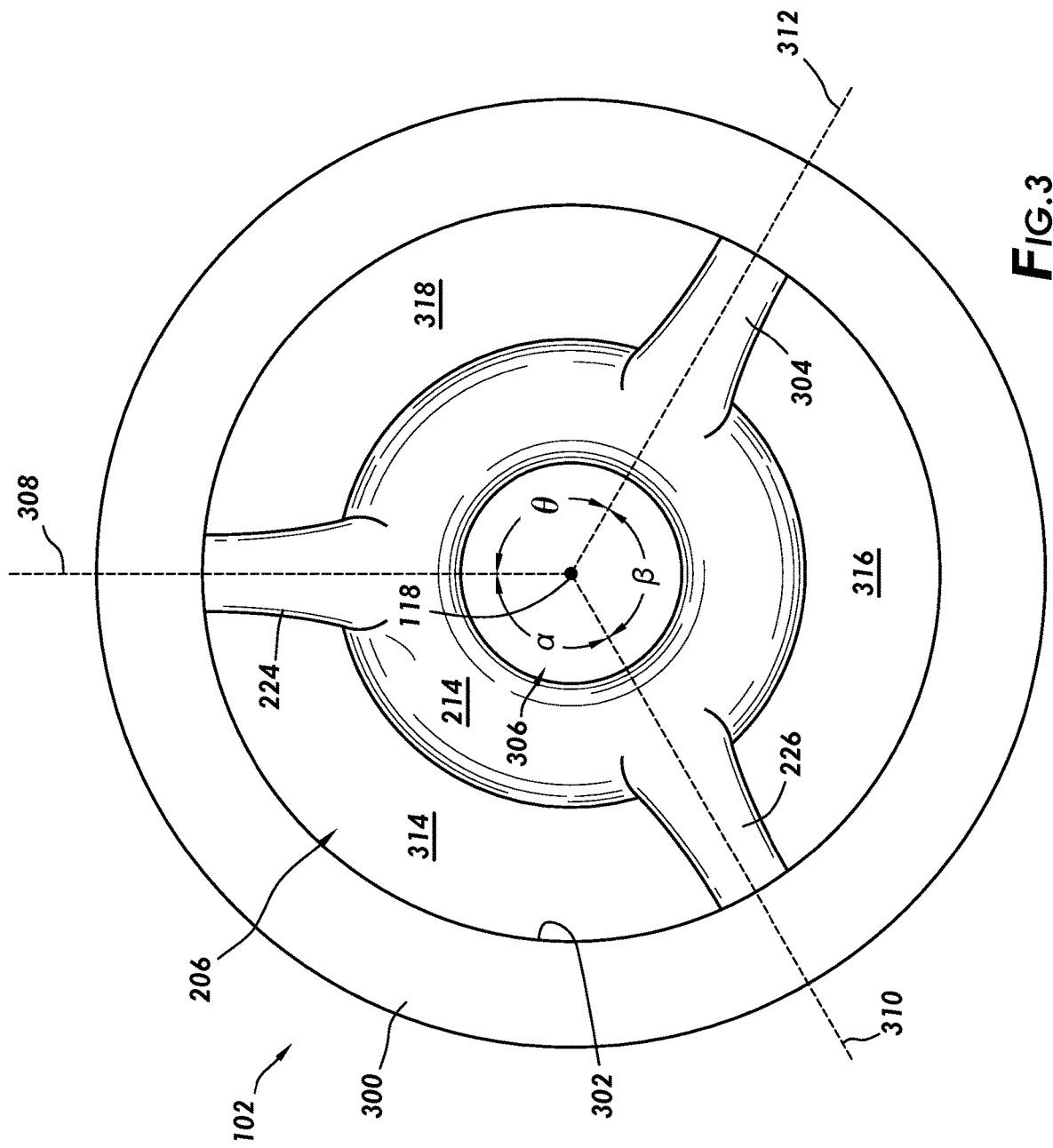
FIG. 3 shows a cross sectional view of the polymeric sleeve taken across the proximal volume looking toward the vent end, in accordance with at least some embodiments.

FIG. 3 shows a cross sectional view of the polymeric sleeve 102 taken within the proximal volume 218 looking toward the vent end 204, in accordance with at least some embodiments. In particular, visible in FIG. 3 is the outer wall 300 of the polymeric sleeve 102, and an inside surface of the outer wall 300 defines the internal surface 302 of the internal chamber 206. In the view of FIG. 3, the proximal flange 214 is shown suspended with the internal chamber 206. The proximal flange 214 is suspended within the internal chamber 206 by the stanchion 224, the stanchion 226, and a stanchion 304. In the view of FIG. 3, the longitudinal central axis 118 is perpendicular to the plane of the page, and thus is shown as a single dot. FIG. 3 further shows three example radials extending from the longitudinal central axis 118 in three distinct radial directions. The radials are aligned with the three example stanchions 224, 226, and 304. More particularly, each stanchion extends along a radial direction relative to the longitudinal central axis 118, and each stanchion is coupled to a respective portion of the internal surface 302. Considering stanchion 224, stanchion 224 extends from the proximal flange 214 to the internal surface 302 of the internal chamber 206 along a radial direction shown by radial line 308. Stanchion 226 extends from the proximal flange 214 to the internal surface 302 along a radial direction shown by radial line 310. Stanchion 304 extends from the proximal flange 214 of the internal chamber 206 along a radial direction shown by radial line 312. In example embodiments, the radial lines 308 and 310, and thus the directions that the stanchions 224 and 226 extend, form an angle α of at least 90 angular degrees, and as shown about 120 angular degrees. The radial lines 310 and 312, and thus the directions that the stanchions 226 and 304 extend, form an angle β of at least 90 angular degrees, and as shown about 120 angular degrees. Finally, the radial lines 312 and 308, and thus the directions that the stanchions 304 and 224 extend, form an angle θ of at least 90 angular degrees, and as shown about 120 angular degrees. In example cases where exactly two stanchions are present the directions that the stanchions extend may form an angle of 180 angular degrees.

Still referring to FIG. 3, the example proximal flange 214 has a thickness, as do the stanchions, and thus the combination of stanchions and the proximal flange 214 form a plurality of interstitial volumes. In particular, the stanchion 224, the stanchion 226, the internal surface 302, and the proximal flange 214 define an interstitial volume 314. The stanchion 226, the stanchion 304, the internal surface 302, and the proximal flange 214 define another interstitial volume 316. The stanchion 304, the stanchion 224, the internal surface 302, and the proximal flange 214 define yet another interstitial volume 318. During use of the system 100, and in particular during insertion, the proximal flange 214 will tend to displace along the longitudinal central axis 118 toward the vent end 204 (FIG. 2). The interstitial volumes 314, 316, and 318 enable displaced air to move proximally during insertion. Similarly, during extraction, the proximal flange 214 will tend to move proximally. The interstitial volumes 314, 316, and 318 enable displaced air to move distally during extraction.

Because of the location of the "cut" to create the view of FIG. 3, the proximal flange 214 is visible and thus is the topic of discussion. However, additional flanges (e.g., the distal flange 216 (FIG. 2)) may be present. Each additional flange will likewise have its associated two or more stanchions, with the radial offset based on the number of stanchions (e.g., two stanchions having 180 angular degrees of offset, three stanchions having 120 angular degrees of offset, four stanchions having 90 angular degrees of offset). Moreover, each flange will define a plurality of interstitial volumes between stanchions (e.g., two stanchions and two interstitial volumes, three stanchions and three interstitial volumes, four stanchions and four interstitial volumes). Further still, in embodiments in which more than one flange is present, the flanges need not have the same number of stanchions. The specification contemplates all such variations.

The example proximal flange 214 defines a through-hole or aperture 306. In accordance with at least some embodiments, the aperture 306 defines an inside diameter. In some cases, the inside diameter of the aperture 306 is about the same as the diameter D3 (FIG. 2) of the main aperture 112. In other cases, the inside diameter of the aperture 306 may be about twice the diameter D3. Regardless, the inside diameter of the aperture 306 is designed and constructed such that, during insertion, the diameter expands slightly to provide an area of increased inward circumferential pressure on the penis. In one example, each flange has an aperture having the same inside diameter. In other cases, the inside diameter of each flange may be different based on the position of the flange longitudinal along the longitudinal central axis 118. For example, the inside diameter of the aperture 306 of the proximal flange 214 may be smaller than the inside diameter of the distal flange 216 (FIG. 2), or vice versa. The specification now turns to example methods of creating the polymeric sleeves.

Figure 4:
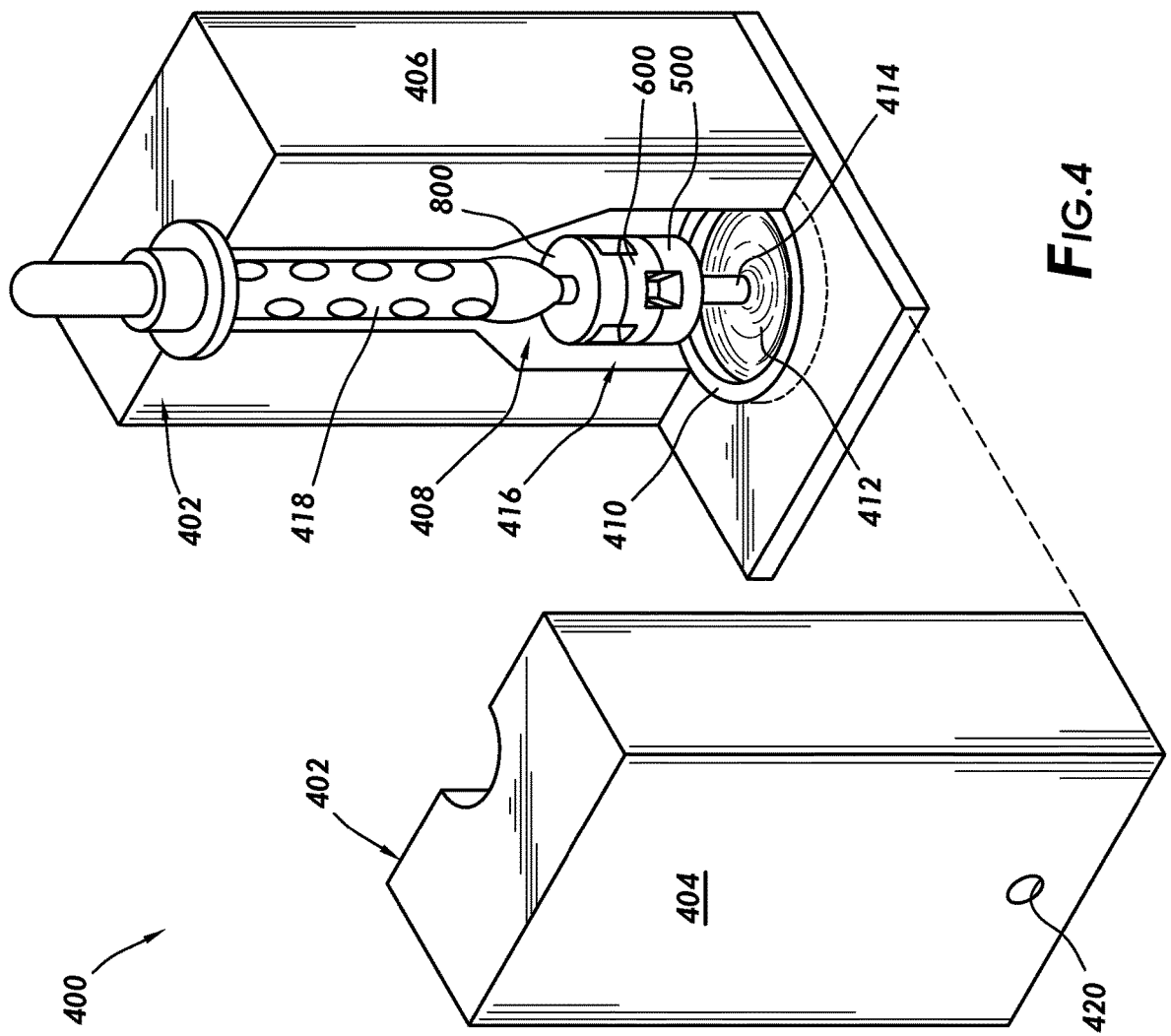
FIG. 4 shows a perspective view of a mold system in accordance with at least some embodiments.

FIG. 4 shows a perspective view of a mold system 400 in accordance with at least some embodiments. In particular, FIG. 4 shows an outer mold assembly 402 comprising first mold member 404 and second mold member 406. Each mold member 404 and 406 defines an interior surface, but in the view of FIG. 4 only the interior surface 408 of mold member 406 is visible. The interior surface 408 of mold member 406 forms half a negative image of the exterior surface of the polymeric sleeve 102 (FIG. 1) spanning from just after the insertion end 106 (FIG. 1) to the vent end 204 (FIG. 2). Likewise, the interior surface of the mold member 404 forms the other half of the negative image of the exterior surface of the polymeric sleeve 102 from just after the insertion end 106 to the vent end 204.

The mold system 400 further comprises a lower mold component 410 placed in operational relationship to the interior surfaces defined by the outer mold assembly 402. The lower mold component 410 structurally defines a negative image of the outer portions of the insertion end 106 of the polymeric sleeve 102, and thus forms a basin-like volume 412. In some cases, and as shown, the basin-like volume 412 may merely define the main aperture 112 (FIG. 1). However, in other cases the lower mold component may form the negative image of an anatomical structure to be created on the insertion end 106 (e.g., female genitalia). The lower mold component 410 also defines a rod or stem 414 that defines the first portion 208 (FIG. 2) of the main passageway 114 in the completed polymeric sleeve 102. A disk assembly 416 is stacked on top of an upper end of the stem 414, and the example disk assembly 416 defines the negative image of the internal chamber along with the flanges and stanchions for each flange. Stated otherwise, during the injection molding process the disk assembly 416 resides within a volume such that no polymeric material may fill and/or occupy the volume, and the locations in which the polymeric material does not fill or reside forms the internal chamber, the interstitial volumes, and the aperture(s) through the flanges. A rod member 418 couples to and/or stacks on top of the disk assembly 416. An exterior surface of the example rod member 418 defines the negative image of the interior surface of the second portion 212 (FIG. 2) of the main passageway 114 through the polymeric sleeve 102. In the example shown, the rod member 418 has the negative image of features to be produced in the second portion 212 of the main passageway 114, but in other cases the second portion 212 may be smooth.

In some example systems, the various mold components, including the lower mold component 410, the disk assembly 416, and the rod member 418 may be themselves cast or milled from metallic material, such as aluminum. However, other materials (e.g., high density plastics) may also be used.

The molding process may involve stacking the disk assembly 416 on the stem 414 in the lower mold component 410, and coupling the rod member 418 to the top of the disk assembly 416. The outer mold assembly 402 is closed around the various components and held in place in some fashion. The polymeric material in liquid form is injected through an injection port into the volume defined by the interior surface 408, such as injection through injection aperture 420. The polymeric material in liquid form fills the volume defined by the interior surface 408, displacing the air, and then the polymeric material is allowed to cure. Once cured, the outer mold assembly 402 is again opened, the rod member 418 withdrawn from the main passageway, the disk assembly 416 is separated into individual disk members (discussed more below) and each disk member removed either through the main aperture 112 (FIG. 1) or through the vent end 204 (FIG. 2). Trimming of the polymeric sleeve 102 may be performed, such as to remove the polymeric material that cured inside the injection aperture, and any mold seams or marks formed by the interface of the outer mold assembly. In some cases, the polymeric sleeve 102 created may be treated with compound to reduce surface tension (such as by application of talcum powder). The specification now turns to a more detailed description of example disk assembly 416.

Figure 5:
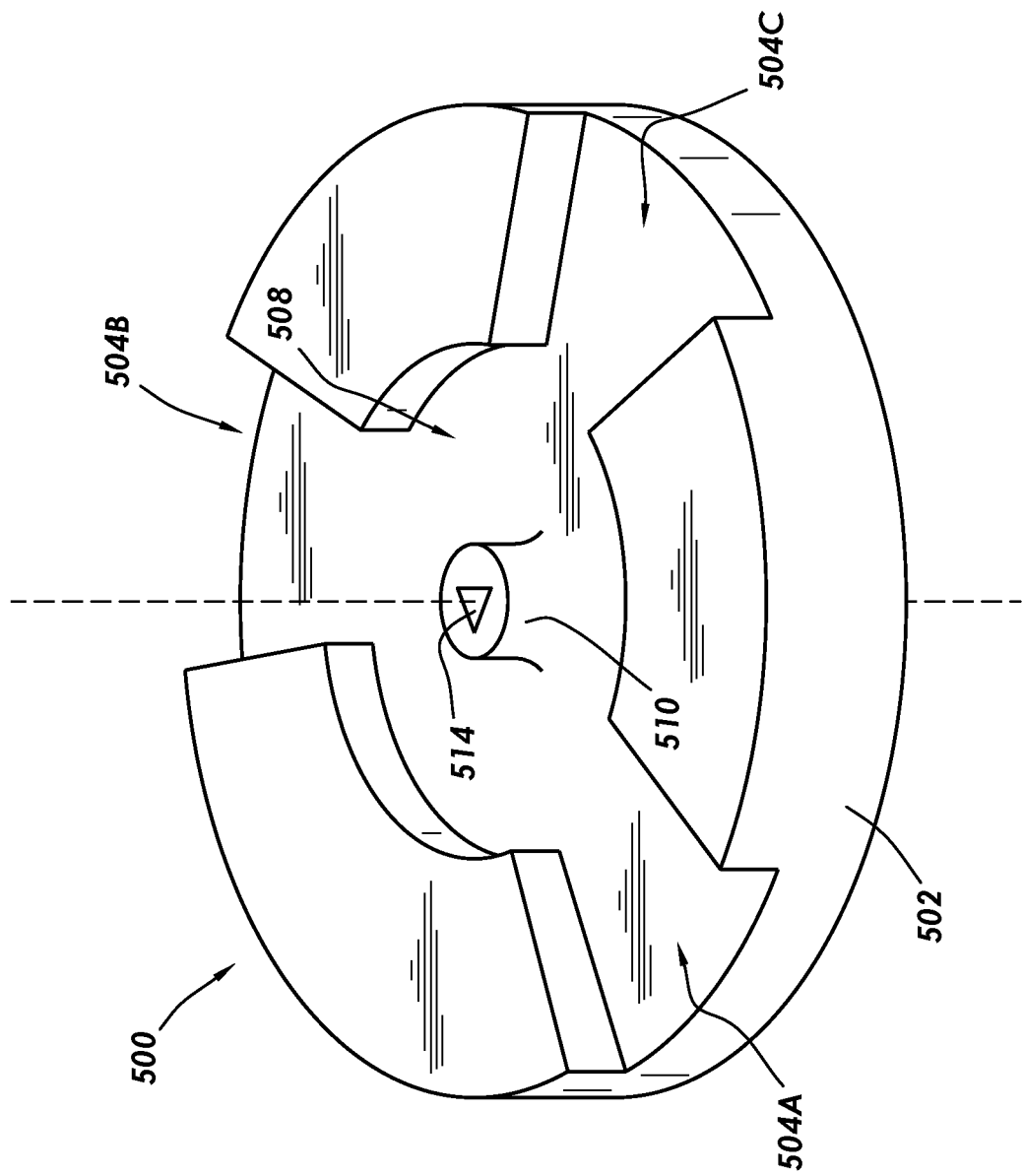
FIG. 5 shows a perspective view of a lower disk member in accordance with at least some embodiments.

FIG. 5 shows a perspective view of a lower disk member in accordance with at least some embodiments. In particular, the lower disk member 500 defines an exterior surface 502 and an upper mold surface. The example exterior surface 502 defines the negative image of a portion of the internal chamber 206, and in the example the exterior surface 502 defines the proximal volume 218 (FIG. 2) and at least a portion of each of the interstitial volumes 314, 316, and 318 (FIG. 3). The example lower disk member 500 defines three channels 504A, 504B, and 504C. The channels 504 extend from the exterior surface 502 to a central area 508. The lower disk member 500 also defines a protrusion or butte 510, which butte 510 may be centered within the mold surface.

The channels 504A, 504B, and 504C are the negative image of portions of the stanchions that suspend and support the proximal flange 214. The central area 508 is a negative image of a portion of the proximal flange 214, in the example case being a toroid with the square or rectangular cross-section. The butte 510 is the negative image of at least a portion of the aperture 306 (FIG. 3). During the injection molding process the polymeric material, in liquid form, is forced into the channels 504 and central area 508. Once cured, the polymeric material thus forms the stanchions 224, 226, and 304 and the proximal flange 214. It follows that the stanchions 224, 226, and 304 and the proximal flange 214 are not individual components assembled into a system; rather, the stanchions and flange are simultaneously formed and thus are integrated components. Thus, the stanchions and flange may be referred to as stanchion members and a flange member.

Still referring to FIG. 5. In some cases a particular rotational alignment of the lower disk member 500 with the medial disk member is used, and thus the lower disk member 500 may have one or more features that assist in the alignment process. For example, the lower disk member 500 has an alignment feature 514 defined in butte 510. The example alignment feature 514 is an aperture defining a triangular cross-section, though other cross-sectional shapes may be used (e.g., square, rectangle, hexagon). A corresponding feature of the medial disk member (discussed more below) has a shape that telescopes into the example alignment feature, thus ensuring proper rotational alignment. Other alignment features may be equivalently used. The specification now turns to the medial disk member.

Figure 6:
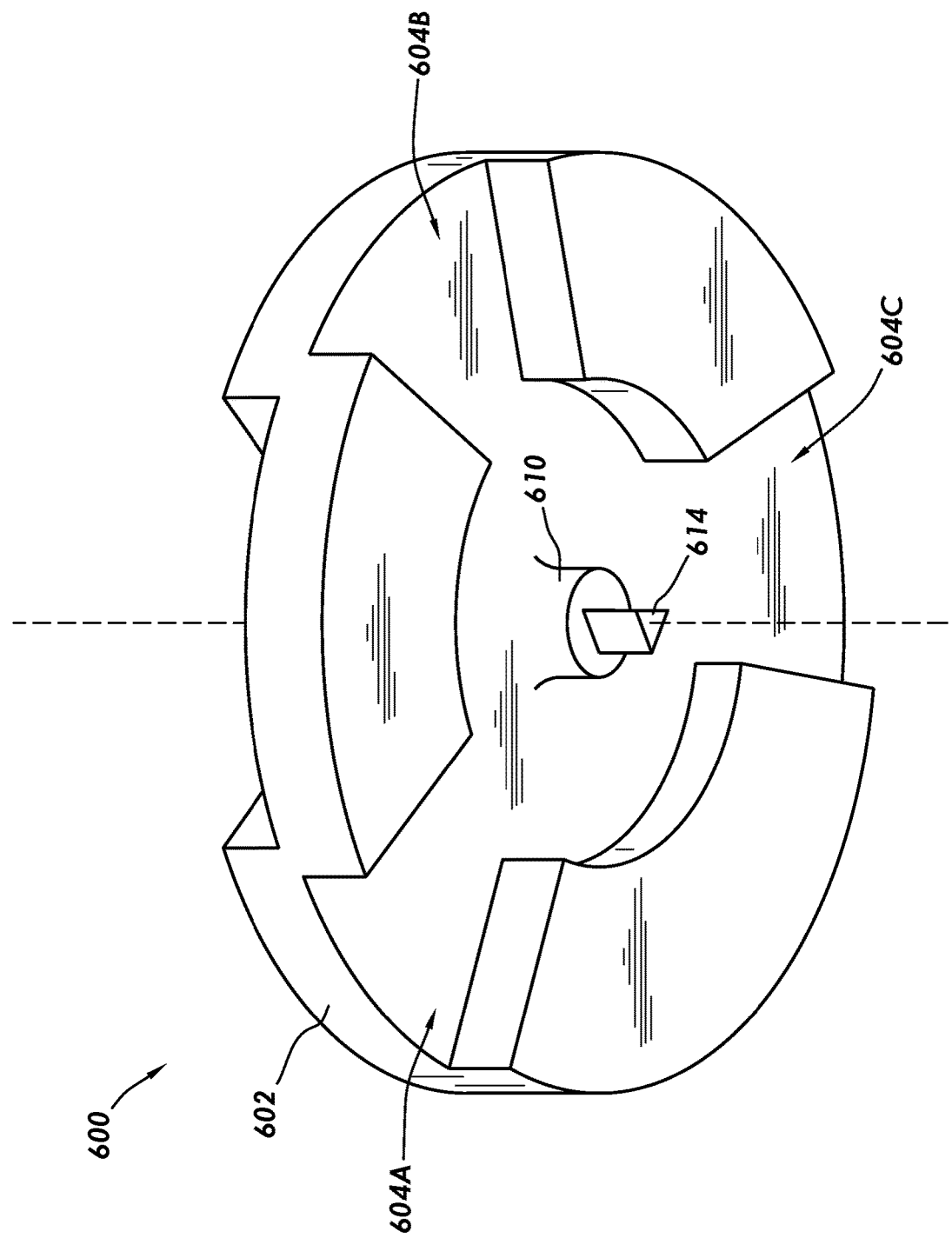
FIG. 6 shows a bottom perspective view of a medial disk member in accordance with at least some embodiments.

FIG. 6 shows a bottom perspective view of a medial disk member in accordance with at least some embodiments. In particular, the medial disk member 600 defines an exterior surface 602 and two mold surfaces—a lower mold surface defined on the lower surface shown, and an upper mold surface defined on the upper surface (not visible, but see FIG. 7). The example exterior surface 602 defines the negative image of portions of the interstitial volumes 314, 316, and 316 (FIG. 3), the medial volume 220 (FIG. 2), and portions of interstitial volumes associated with the example distal flange 216 (FIG. 2).

In creating the disk assembly 416, the medial disk member 600 is configured to stack on to and abut the lower disk member 500. The example medial disk member 600 defines lower channels 604A, 604B, and 604C. The lower channels 604A, 604B, and 604C correspond to channels 504A, 504B, and 504C of the lower disk member 500 (FIG. 5). The lower channels 604 are the negative image of portions (e.g., the distal portions) of the stanchions 224, 226, and 305 that suspend and support the proximal flange 214. Thus, the combination of the medial disk member 600 and the lower disk member 500 define the channels that create the stanchions 224, 226, and 304 for the proximal flange 214 (FIG. 2). In yet still other cases, however, the lower surface of the medial disk member 600 may be flat, and thus defining only the upper surface of the channels that create the stanchions for the proximal flange 214.

The medial disk member 600 further defines, on the lower surface, a central area 608. The central area 608 is a negative image of a portion of the proximal flange 214, in the example case being a toroid with the square or rectangular cross-section. The medial disk member 600 further defines, on the lower surface, a protrusion or butte 610, which butte 610 may be centered within the mold surface. The butte 610 is the negative image of at least a portion of the aperture 306 (FIG. 3). During the injection molding process the polymeric material, in liquid form, is forced into the channels 604 and central area 608. Once cured, the polymeric material thus forms the stanchions 224, 226, and 304 and the proximal flange 214. In yet still other cases, however, the lower surface of the medial disk member 600 may be flat, and thus defining only the upper surface of the proximal flange 214.

Still referring to FIG. 6. In some cases a particular rotational alignment of the lower disk member 500 with the medial disk member 600 is used, and thus the medial disk member 600 may also have one or more features that assist in the alignment process. For example, the lower mold surface of the medial disk member 600 has an alignment feature 614 associated with the butte 610. The example alignment feature 614 is a protrusion defining a triangular cross-section, though other cross-sectional shapes may be used. The example alignment feature 614 is designed and constructed to telescope into the alignment feature 514 of the lower disk member 500 (FIG. 5). Other alignment features may be equivalently used. The specification now turns to the upper mold surface of the medial disk member 600.

Figure 7:
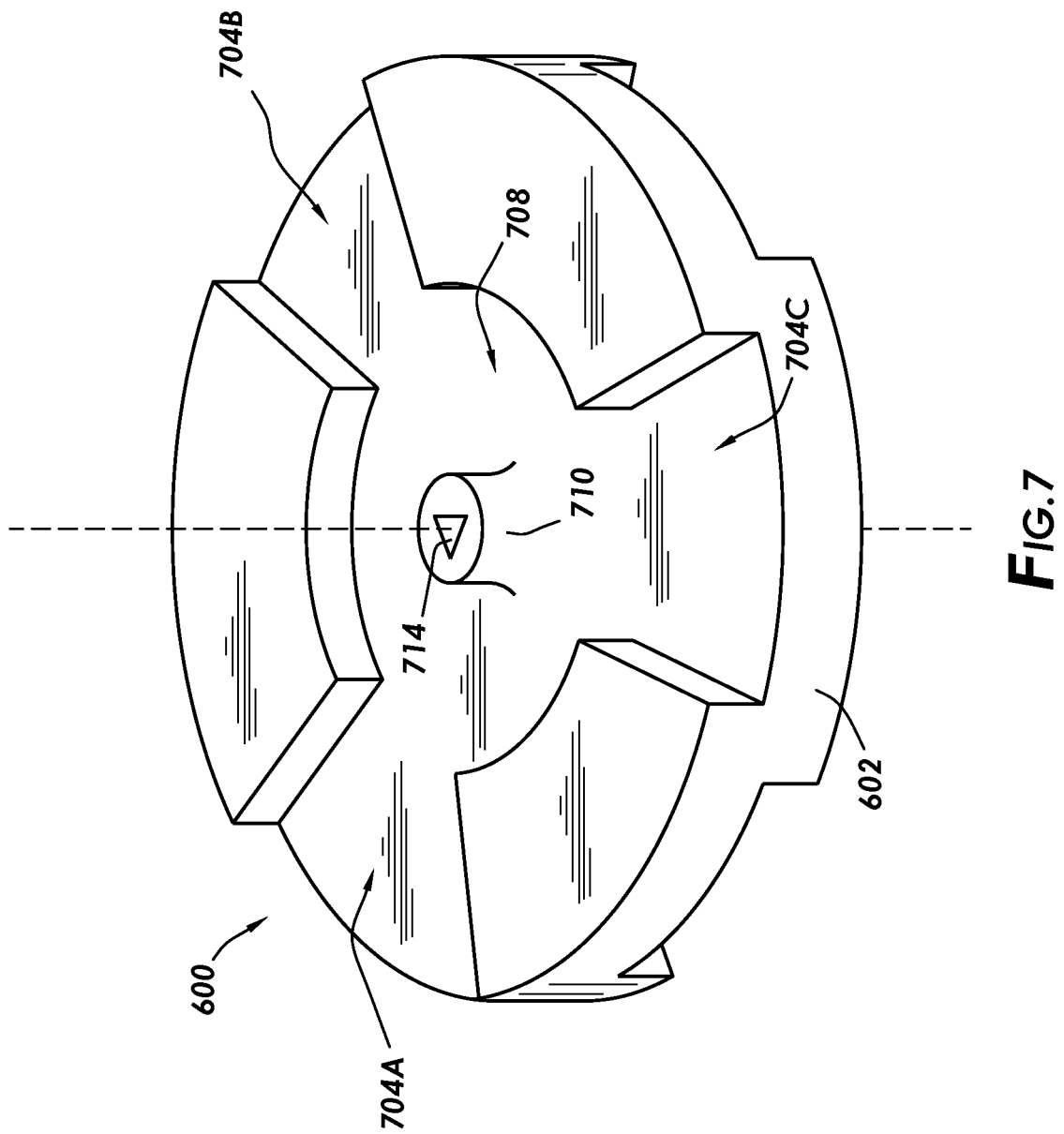
FIG. 7 shows an upper perspective view of a medial disk member in accordance with at least some embodiments.

FIG. 7 shows a top perspective view of a medial disk member in accordance with at least some embodiments. Again, the medial disk member 600 defines an upper mold surface. The upper mold surface of the medial disk member 600 defines three channels 704A, 704B, and 704C. The channels 704 extend from the exterior surface 602 to a central area 708. The upper surface of the medial disk member 600 also defines a protrusion or butte 710, which butte 710 may be centered within the upper mold surface.

The channels 704A, 704B, and 704C are the negative image of portions of the stanchions (e.g., stanchions 228 and 230) that suspend and support the distal flange 216. The central area 708 is a negative image of a portion of the distal flange 216, in the example case being a toroid with the square or rectangular cross-section. The butte 710 is the negative image of at least a portion of the aperture through the distal flange 216. During the injection molding process, the polymeric material, in liquid form, is forced into the channels 704 and central area 708. Once cured, the polymeric material thus forms the stanchions (e.g., stanchions 228 and 230) and the distal flange 216. It follows that the stanchions and the distal flange 216 are not individual components assembled into a system; rather, the stanchions and distal flange are simultaneously formed and thus are integrated components. Thus, again the stanchions and flange may be referred to as stanchion members and a flange member.

Still referring to FIG. 7. In some cases a particular rotational alignment of the medial disk member 600 with the upper member is used, and thus the upper mold surface of the medial disk member 600 may have one or more features that assist in the alignment process. For example, the upper mold surface of the medial disk member 600 has an alignment feature 714 defined in butte 710. The example alignment feature 714 is an aperture defining a triangular cross-section, though other cross-sectional shapes may be used. A corresponding feature of the upper disk member (discussed more below) has a shape that telescopes into the example alignment feature, thus ensuring proper rotational alignment. Other alignment features may be equivalently used. The specification now turns to the upper disk member.

Figure 8:
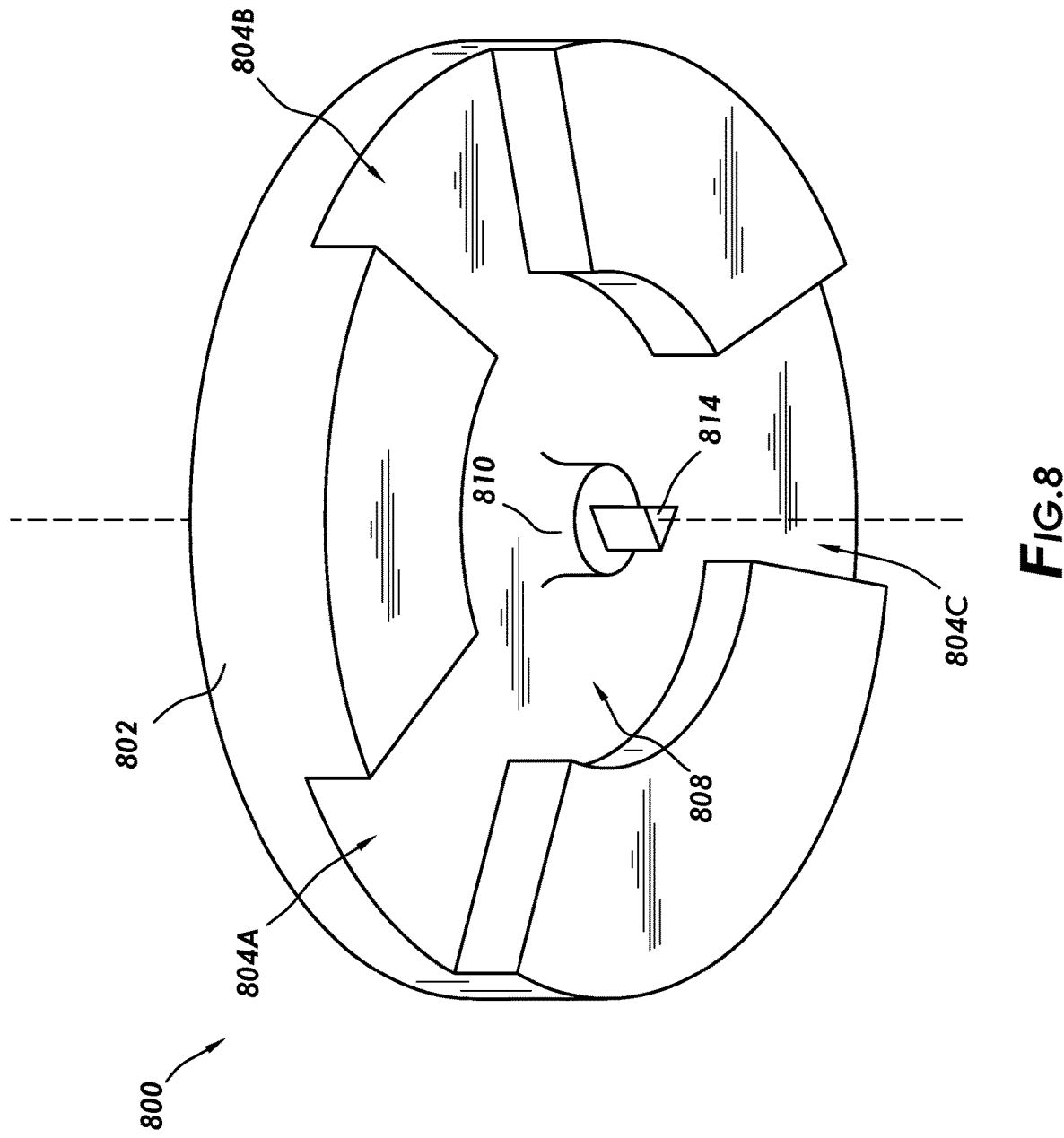
FIG. 8 shows a bottom perspective view of an upper disk member in accordance with at least some embodiments.

FIG. 8 shows a bottom perspective view of an upper disk member in accordance with at least some embodiments. In particular, the upper disk member 800 defines an exterior surface 802 and a lower mold surface. The example exterior surface 802 defines the negative image of a portion of the interstitial volumes between stanchions of the distal flange 216, as well as the distal volume 222 (FIG. 2).

In creating the disk assembly, the upper disk member 800 is configured to stack on to and abut the upper surface of the medial disk member 600. The example upper disk member 800 defines channels 804A, 804B, and 804C. The channels 804A, 804B, and 804C correspond to channels 704A, 704B, and 704C on the upper mold surface of the medial disk member 600 (see FIG. 5). The channels 804 are the negative image of portions (e.g., the distal portions) of the stanchions (e.g., stanchions 228 and 230) that suspend and support the distal flange 216. Thus, the combination of the upper mold surface of the medial disk member 600 and the upper disk member 800 define the channels that create the stanchions (e.g., stanchions 228 and 230) for the distal flange 216 (FIG. 2). In yet still other cases, however, the lower surface of the upper disk member 800 may be flat, and thus defining only the upper surface of the channels that create the stanchions for the distal flange 216.

The upper disk member 800 further defines, on the lower mold surface, a central area 808. The central area 808 is a negative image of a portion of the distal flange 216, in the example case being a toroid with the square or rectangular cross-section. The upper disk member 800 further defines, on the lower mold surface, a protrusion or butte 810, which butte 810 may be centered within the mold surface. The butte 810 is the negative image of at least a portion of the aperture through the distal flange 216. During the injection molding process the polymeric material, in liquid form, is forced into the channels 804 and central area 808. Once cured, the polymeric material thus forms the stanchions (e.g., stanchions 228 and 230) and the distal flange 216. In yet still other cases, however, the lower surface of the upper flange member 800 may be flat, and thus defining only the upper surface of the stanchions and proximal flange 214.

Still referring to FIG. 8. In some cases a particular rotational alignment of the medial disk member 600 with the upper disk member 800 is used, and thus the upper disk member 800 may also have one or more features that assist in the alignment process. For example, the lower surface of the upper disk member 800 has an alignment feature 814 defined on the butte 810. The example alignment feature 814 is a protrusion defining a triangular cross-section, though other cross-sectional shapes may be used. The example alignment feature 814 is designed and constructed to telescope into the alignment feature 714 on the upper surface of the medial disk member 600). Other alignment features may be equivalently used.

Returning to FIG. 4. In the example embodiments, the disk assembly 416 comprises the lower disk member 500, the medial disk member 600, and the upper disk member 800. In particular, the disk assembly 416 may be assembled by abutting the lower disk member 500 against a medial disk member 600, and abutting the medial disk member 600 against the upper disk member 800, with all three disk members being coaxially aligned. In one example, the lower disk member 500 and the medial disk member 600 define the negative image of at least two stanchions and the proximal flange 214 (FIG. 2), and the medial disk member 600 and the upper disk member 800 define a negative image of at least two stanchions and the distal flange 216. In a specific example, the lower disk member 500 and the medial disk member 600 define the negative image of three stanchions and the proximal flange 214, and the medial disk member 600 and the upper disk member 800 define a negative image of three stanchions and the distal flange 216.

Figure 9:
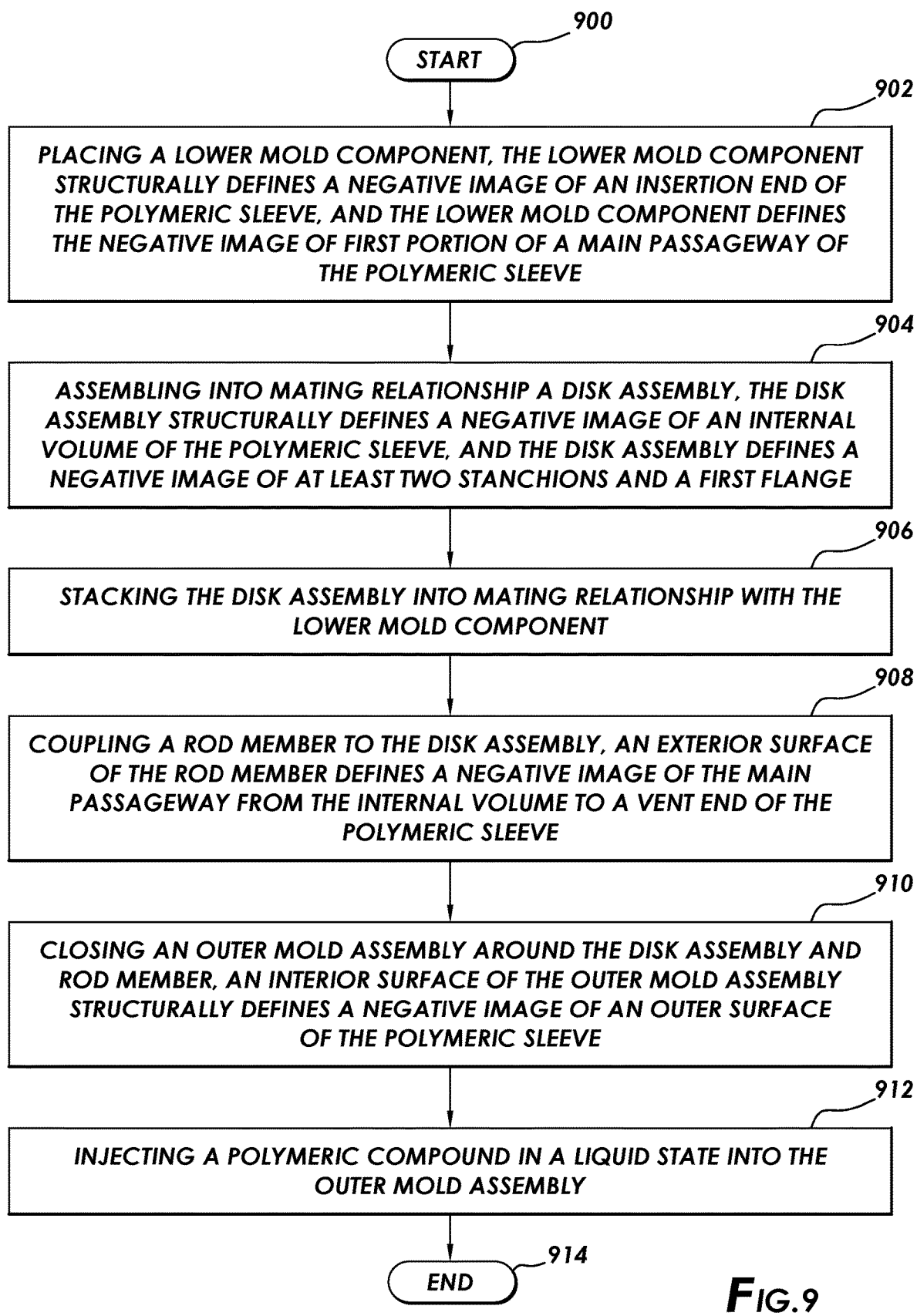
FIG. 9 shows a method in accordance with at least some embodiments.

FIG. 9 shows a method in accordance with at least some embodiments. In particular, the method starts (block 900) and comprises: placing a lower mold component, the lower mold component structurally defines a negative image of an insertion end of the polymeric sleeve, and the lower mold component defines the negative image of first portion of a main passageway of the polymeric sleeve (block 902); assembling into mating relationship a disk assembly, the disk assembly structural defines a negative image of an internal volume of the polymeric sleeve, and the disk assembly defines a negative image of at least two stanchions and a first flange (block 904); stacking the disk assembly into mating relationship with the lower mold component (block 906); coupling a rod member to the disk assembly, an exterior surface of the rod member defines a negative image of the main passageway from the internal volume to a vent end of the polymeric sleeve (block 908); closing an outer mold assembly around the disk assembly and rod member, an interior surface of the outer mold assembly structurally defines a negative image of an outer surface of the polymeric sleeve (block 910); and injecting a polymeric compound in a liquid state into the outer mold assembly (block 912). Thereafter, the method ends (block 914)

The above discussion is meant to be illustrative of the principles and various embodiments of the present invention. Numerous variations and modifications will become apparent to those skilled in the art once the above disclosure is fully appreciated. For example, though referred to as the vent end 204, in some cases the system may be designed and constructed for insertion from either direction, and thus reference to the vent end 204 shall not be read to limit the operational aspects to just venting. As another example, a flange may be a triangular volume, or a cuboid, with corners that abut the inside surface of the internal volume and thus define the stanchions. It is intended that the following claims be interpreted to embrace all such variations and modifications.

What is claimed is:

1. A system comprising:
    a polymeric sleeve comprising:
        an elongate body that defines a first end, a second end opposite the first end, and a longitudinal central axis;
        a main passageway through the elongate body along the longitudinal central axis, the main passageway extends from the first end to the second end, and the main passageway defines a first aperture on the first end and a second aperture on the second end;
        an internal chamber defined within the main passageway between the first aperture and the second aperture;
        a first flange disposed within the internal chamber at a first position along the longitudinal central axis, the first flange defines an aperture at least partially aligned with the longitudinal central axis;
        a first stanchion extending from the first flange along a first radial direction relative to the longitudinal central axis, the first stanchion coupled to an inside surface of the internal chamber;
        a second stanchion extending from the first flange along a second radial direction relative to the longitudinal central axis, the second stanchion coupled to an inside surface of the internal chamber; and
        the first and second stanchions suspend the first flange within the internal chamber.

2. The system of claim 1 further comprising a first interstitial volume defined between the inside surface of the internal chamber, the first stanchion, and the second stanchion.

3. The system of claim 1 wherein the first radial direction and the second radial direction form an angle of at least 90 angular degrees.

4. The system of claim 3 wherein the first radial direction and the second radial direction form an angle of 180 angular degrees.

5. The system of claim 1 further comprising a third stanchion extending from the first flange along a third radial direction relative to the longitudinal central axis, the third stanchion coupled to the inside surface of internal chamber.

6. The system of claim 5
    wherein the first radial direction and the second radial direction form an angle of 120 angular degrees; and
    wherein the second radial direction and the third radial direction form an angle of 120 angular degrees.

7. The system of claim 5 further comprising:
    a first interstitial volume defined between the inside surface of the internal chamber, the first stanchion, and the second stanchion;
    a second interstitial volume defined between the inside surface, the second stanchion, and third stanchion; and
    a third interstitial volume defined between the inside surface, the third stanchion, and the first stanchion.

8. The system of claim 1 further comprising:
    a second flange disposed within the internal chamber at a second position along the longitudinal central axis;
    a third stanchion extending from the second flange along a third radial direction relative to the longitudinal central axis, the third stanchion coupled to the inside surface;

a fourth stanchion extending from the second flange along a fourth radial direction relative to the longitudinal central axis, the fourth stanchion coupled to the inside surface; and the third and fourth stanchions suspend the second flange within the internal chamber.

9. The system of claim 1 further comprising:

a third stanchion extending from the first flange along a third radial direction relative to the longitudinal central axis, the third stanchion coupled to the inside surface;

a second flange disposed within the internal chamber at a second position along the longitudinal central axis;

a fourth stanchion extending from the second flange along a fourth radial direction relative to the longitudinal central axis, the fourth stanchion coupled to the inside surface;

a fifth stanchion extending from the second flange along a fifth radial direction relative to the longitudinal central axis, the fifth stanchion coupled to the inside surface; and a sixth stanchion extending from the second flange along a sixth radial direction relative to the longitudinal central axis, the sixth stanchion coupled to the inside surface.

10. The system of claim 9 further comprising:

the first radial direction and the second radial direction form an angle of 120 angular degrees;

the second radial direction and the third radial direction form an angle of 120 angular degrees;

the fourth radial direction and the fifth radial direction form an angle of 120 angular degrees;

the fifth radial direction and the sixth radial direction form an angle of 120 angular degrees; and the first radial direction and the third radial direction form an angle of 60 angular degrees.

11. The system of claim 1 further comprising an outer cover of rigid material that defines an interior volume, wherein the polymeric sleeve is at least partially disposed within the outer cover.

* * * * *